(12) United States Patent
Chang et al.

(10) Patent No.: US 7,378,100 B2
(45) Date of Patent: May 27, 2008

(54) FUSION PROTEIN FOR INHIBITING CERVICAL CANCER

(75) Inventors: Hsui-Kang Chang, Taipei (TW); Chao-We Liao, Jhunan Township, Miaoli County (TW); Wen-Fang Cheng, Taipei (TW)

(73) Assignee: Healthbanks Biotech Co., Ltd., Taipei (TW)

( * ) Notice: Subject to any disclaimer, the term of this patent is extended or adjusted under 35 U.S.C. 154(b) by 287 days.

(21) Appl. No.: 11/206,138

(22) Filed: Aug. 18, 2005

(65) Prior Publication Data

US 2006/0039919 A1 Feb. 23, 2006

(30) Foreign Application Priority Data

Aug. 20, 2004 (TW) ............................... 93125128 A (51) Int. Cl.
*A61K 39/12* (2006.01)
(52) U.S. Cl. ........................................ 424/204.1; 435/6
(58) Field of Classification Search ............. 424/204.1; 435/6
See application file for complete search history.

(56) References Cited

U.S. PATENT DOCUMENTS 5,705,163 A 1/1998 Pastan et al.
6,214,541 B1 4/2001 Zentgraf et al.
2004/0086845 A1* 5/2004 Wu et al. ....................... 435/5
2004/0247617 A1 12/2004 Liao et al.

FOREIGN PATENT DOCUMENTS

WO WO 03/080669 A2 10/2003
WO WO 03/085085 * 10/2003

OTHER PUBLICATIONS

Hung et al. Cancer Research, May 2001, vol. 61, pp. 3698-3703.*
Y.Qin, et al. "Human papillomavirus type 16 E7 peptide38-61 linked with an immunoglobulin G fragment provides protective immunity in mice", Gynecologic Oncology, 2005, vol. 96, pp. 475-483.
C. Liao, et al., "Fusion Protein Vaccine by Domains of Bacterial Exotoxin Linked with a Tumor Antigen Generates Potent Immunologic Responses and Antitumor Effects", Cancer Res, 2005, vol. 65, No. 19, pp. 9089-9098.

* cited by examiner

*Primary Examiner*—Ali R. Salimi
(74) *Attorney, Agent, or Firm*—Bacon & Thomas, PLLC (57) ABSTRACT

A fusion protein for inhibiting cervical cancer is disclosed, which comprises a peptide sequence of human papillomavirus type 16, a peptide translocating peptide for translocation, and a peptide within a carboxyl terminal fragment. The present invention further comprising a composition of antibody, which conjugates to E7 peptide, wherein the nucleotide sequence corresponding to the amino acid sequence of the E7 peptide is shown as SEQ. ID. NO.1.

22 Claims, 9 Drawing Sheets

Number of pulmonary tumor nodule (Mean+SEM)

Naive / PE(ΔIII)-E7-KDEL3 one time / PE(ΔIII)-E7-KDEL3 two times / PE(ΔIII)-E7-KDEL3 three times

FUSION PROTEIN FOR INHIBITING CERVICAL CANCER

BACKGROUND OF THE INVENTION

1. Field of the Invention

The present invention relates to a fusion protein, more particularly, to a fusion protein for inhibiting cervical cancer induced or caused by HPV type 16 and pharmaceutical compositions thereof.

2. Description of Related Art

Currently, the incidence ratio of cervical cancer has remained high among all woman cancer patients. There are no any obvious symptoms of general variation of cervical epithelium or early cervical cancer. Although cervical cancer can be successfully treated in its early stages, prevention is still much better than treatment. Therefore, the researchers in this field have been making effort to find out the most efficient way to prevent cervical cancer.

It is already proved that human papillomavirus, HPV is highly related with cervical cancer. Some types (e.g. type 16, or 18) of DNA sequence of HPV had been found in cervical cancer cells, about 75%~100%, but it is still not clear what the mechanism is in causing the cancer. Lately, research has found that the early gene product of virus—protein E6 and E7 of highly dangerous type 16, 18 and 31 of HPV easily combines with the product of genes Rb and p53 and thus reduce the ability of anti-tumor agent. This explains that HPV is not functioning alone when causing cancer but is assisted by environmental factors. Moreover, E7 protein expresses continuously in cervical cancer cells and carcinoma tissues. E7 protein also plays an important role in the process of maintaining shifted malignant tissue phenotype.

The cancer immune therapy is mainly displayed with cell-mediated immunization, assisted by humoral immunization. Cells involved in cell-mediated immunization are cytotoxic T lymphocytes (CTL), NK and macrophages. CTL is triggered by interlukin-2, and then identified by T cells. The major histocompatibility complex (MHC) on the cancer cells with antigen present appears and releases lysozyme to destroy the cancer cells and restrain the proliferation of cancer cells. CTL protection is proved to inhibit cancers caused by HPV. Therefore if it is possible to induce the proliferation of the HPV-antigen-specific CTL, for example, CD $8^+$ T lymphocytes, by enhancing complexes of HPV antigen and MHC class I presenting on cancer cells, the strategy of CTL induction with E7 antigen can be able to control carcinoma cell directly and beneficial for immunological prevention and treatment.

It is proved by research that cervical cancer is able to be prevented by vaccine injection. E7 proteins of HPV are highly common in carcinoma tissues or the tissues before carcinoma damage, therefore, E7 protein has the potential for developing as a vaccine. Basically, HPV type 16 and HPV type 18 are serious causes of not only cervical cancer, they are also dangerous factors for inducing lung cancer in females. The carcinogenic proteins E6 and E7 can be transferred to lungs through the circulation of blood and they decompose the anti-tumor proteins produced by gene Rb and p53. Once the anti-tumor genes or the proteins produced by them are deactivated, cancer cells show up. Though the present DNA vaccine does have a long term effect, on the other hand, it has high production costs. The main factor of restrained development in the DNA vaccine is the highly dangerous nature of the virus itself, which mutates easily. Furthermore, when applying E7 protein in gene therapy to cervical cancer, the induced immune response is usually induced weakly because of the weak antigen character of E7 protein of HPV virus. The effect of the prophylaxis and the therapy of cervical cancer are not able to be evaluated because of frail immune response.

Generally, the specific antigen of cancer cells needs to be modified and combined with MHC-I then presented to the cell surface in order to trigger the $CD8^+$ cells and elicit cell-mediated system. The research shows that the HPV type 16 E7 gene can be found in cervical cancer tissues but there is a lack of the specific MHC-I complex to present to the cell surface for showing E7 antigen. Therefore, HPV type 16 E7 protein will not be present to or initiate the cellular immune system of the host cell and then HPV escapes from the detection or monitoring of host. Usually, when E7 protein is injected in vivo, it is considered as external antigens. The E7 vaccination can only be induced the humor immune response thus lowering the effect to elicit cell-mediated immunity. Hence, it is necessary to develop a transportation system of sending the intact foreign protein into cytoplasm and induce effective immune response.

Therefore, it is desirable to provide an fusion protein for inhibiting cervical cancer to mitigate and/or obviate the aforementioned problems.

SUMMARY OF THE INVENTION

A fusion protein for inducing immune response of specific cancers is disclosed, especially to some weak antigen viruses, which do not easily induce immune response. The fusion protein of the present invention can effectively inhibit the proliferation of carcinoma cells and lower the carcinoma level, and moreover can to prevent cancers.

The fusion protein of the present invention is able to induce CTL and antibody protection in vivo, then further is able to destroy the infected cells by presenting the antigen. A pharmaceutical composition for preventing or inhibiting cancer cells induced by human papillomavirus type 16 is also disclosed in the present invention. The pharmaceutical composition of the present invention also comprises a medical compound such as a fusion protein for preventing or inhibiting cancer induced by human papillomavirus type 16, wherein the compound is able to control the proliferation or the increase of carcinoma cells.

The fusion protein, T cell vaccine, or the pharmaceutical composition includes the fusion protein for inhibiting or preventing cancer induced by human papillomavirus type 16 of the present invention comprise: an E7 peptide segment of human papillomavirus type 16; a translocating peptide segment possessing translocation function; and a peptide fragment having a carboxyl terminal section.

The cancer induced by human papillomavirus type 16 can be inhibited or prevented by the fusion protein of the present invention or the pharmaceutical composition thereof. More precisely, the cancer is cervical cancer or lung cancer. In the fusion protein of the present invention, the nucleotide sequence of E7 peptide segment of human papillomavirus type 16 is preferred as SEQ. ID. NO. 1. The peptide fragment can be selected from any known peptide fragment in the art, which has translocation function, and preferably is a part of pseudomonas exotoxin A. The peptide fragment of carboxyl terminal section can be selected from any known sequence of carboxyl terminal section in the art. Preferably, the peptide fragment of carboxyl terminal section is part of pseudomonas exotoxin, and, the peptide fragment of carboxyl terminal section comprises an amino acid sequence of KDEL, the peptide sequence is SEQ.ID.NO. 2.

The preferable amino acid sequence of fusion protein of the present invention is SEQ.ID.NO. 3.

The present invention also discloses an antibody composition, which is combined E7 peptide, wherein the nucleotide sequence corresponding to the E7 peptide is SEQ. ID. NO. 1. The antibody composition of the present invention is able to detect the antigen of E7 peptide in vivo and then binds together in a way of "key and lock".

The fusion protein of the present invention can be applied for inhibiting or preventing the infection of human papillomavirus type 16. The pharmaceutical composition of the present invention can further include an adjuvant for enhancing the medical effect. The adjuvant can be any conventional adjuvant of the art. Preferably, the adjuvant is aluminum gel, oily adjuvant such as Freund's FCA, or FIA, mannide mono-oleate emulsifier, ISA 206, or ISA 720. More preferably, the adjuvant is ISA 206.

The present invention is applied with the property of bacterial exotoxin in order to combine the bacterial exotoxin carried with protein and the surface acceptor of cell membrane of target cell (antigen presenting cell), the protein thus entering the cell and translocating the protein to cytoplasm by its natural ability of bacterial exotoxin; in the mean time, the external protein in cytoplasm can be prepared into small peptide and combined to MHC I or MHC II, and presented at the outside surface of the antigen presenting cell. The cell combined with MHC II or I will be identified by $CD4^+$ cells or $CD8^+$ cells, further induce a series of immune responses, and the immune ability of the fusion protein of the present invention is thus performed.

The pharmaceutical composition of the present invention can selectively comprise any conventional adjuvant, dispersant, humectant (for example: Tween 80) and suspension to produce sterile injection, for example, a sterile injectable composition can be a solution or suspension in a non-toxic parenterally acceptable diluent or solvent, such as a solution in 1,3-butanediol. Among the acceptable vehicles and solvents that can be employed, mannitol or water is preferred. In addition, fixed oils are conventionally employed as a solvent or suspending medium (e.g., synthetic mono- or diglycerides). Fatty acid, (e.g. oleic acid or glyceride derivatives thereof), and pharmaceutically acceptable natural oils (e.g. olive oil or castor oil, especially polyoxyethylated derivatives thereof) can be used in the preparation of injected composition. These oil solutions or suspensions can also contain a long chain alcohol diluent or dispersant, carboxymethyl cellulose, or similar dispersing agents. Other commonly used surfactants such as Tweens, Spans, other similar emulsifying agents, or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, the preferable vector is lactose, or corn starch. Lubricating agents, such as magnesium stearate, are also typically added. For oral administration in a capsule form, the used diluent is preferred to be lactose, or dried corn starch. When aqueous suspensions or emulsions are administered orally, the active ingredient can be suspended or dissolved in an oily phase combined with emulsifying or suspending agents. If necessary, certain sweetening, flavoring, or coloring agents can be added. vector.

The vector in the pharmaceutical composition must be "acceptable" in the sense that it is compatible with the active ingredient of the composition (and preferably, capable of stabilizing the active ingredient) and not deleterious to the subject to be treated. Examples of other vectors include colloidal silicon oxide, magnesium stearate, cellulose, sodium lauryl sulfate, and D&C Yellow # 10.

The fusion protein of the present invention or the pharmaceutical composition thereof can inhibit or prevent the disease induced by the infection of human papillomavirus type 16. Moreover, the concentration of the antibody induced by the fusion protein of the present invention or the pharmaceutical composition in a subject can last for a long time, and further enhance the medical effect.

Other objects, advantages, and novel features of the invention will become more apparent from the following detailed description when taken in conjunction with the accompanying drawings.

BRIEF DESCRIPTION OF THE DRAWINGS

FIG. 1 shows the flow chart for a 8.0-kb plasmid (named pET-E7-KDEL3) encoding PE(ΔIII)-E7-KDELKDELKDEL (named PE(ΔIII)-E7-KDEL3) construction in example 2;

FIG. 2 shows the result of in vivo tumor protection experiments in example 2; 100% of mice receiving PE(ΔIII)-E7-KDEL3 protein remained tumor-free 60 days after TC-1 challenge. In contrast, all of the unvaccinated mice and mice receiving E7, PE(ΔIII), and PE(ΔIII)-E7 protein groups developed tumors within 15 days after tumor challenge;

FIG. 3 shows the numbers of E7-specific IFN-γ-secreting $CD8^+$ T cell precursors in PE(ΔIII)-E7-KDEL3 group in example 6;

FIG. 4 shows the results for evaluation of the PE(ΔIII)-E7-KDEL3 protein enhancing the titer of anti-E7 antibody in example 7;

FIG. 5 shows the numbers of E7-specific CD $8^+$ T lymphocytes secreting from mice vaccinated with fusion proteins of the present invention with or without an adjuvant in example 8;

FIG. 6 shows the anti-tumor effects in mice with or without an adjuvant in example 8;

FIG. 7A shows the pulmonary tumor nodules in the in vivo tumor treatment experiments in example 9, wherein the symbols illustrate: (i) control group, (ii) E7, (iii) PE(ΔIII), (ix) PE(ΔIII)-E7, and (x) PE(ΔIII)-E7-KDEL3);

FIG. 7B shows the anti tumor effects of mice vaccinated with various times of PE(ΔIII)-E7-KDEL3 protein in example 9;

FIG. 8A shows the tumor prevention effects of mice vaccinated with various times of fusion protein in vivo in example 10; and FIG. 8B shows the tumor suppression effects of mice treated with various times of fusion protein in vivo in example 10.

DETAILED DESCRIPTION OF THE PREFERRED EMBODIMENT

EXAMPLE 1

Synthesis of E7 Nucleotide and KDEL Sequence

HPV type 16 E7 protein sequence (NC_001526, SEQ.ID.NO. 3) was found in the database of National Center for Biotechnology Information (NCBI), U.S.A., 98 amino acid were collected in total.

The method disclosed in Taiwan patent application number 92126644 was conducted to express HPV16 E7 protein by E. coli system in large scale. Modification of the nucleotides in the present embodiment is to replace single base of wild type virus sequence with another base that expressed well in E. coli system, allowing target proteins expressed in E. coli the same as that expressed naturally. The modified sequence of HPV16 E7 nucleotide is SEQ.ID.NO. 1.

Eight pairs of primers were used for the synthesis of polynucleotides in the present example. The polynucleotide are synthesized by polymerase chain reaction (PCR). The sequence of all primers are shown in table 1. The sequences underlined represent as complementary fragments to a specific sequences.

At first, F1 and R1 primers are used to perform polyneucleotides synthesis by PCR without DNA template. There are 15 bases designed for complementary to each other at 3' end of the both primers, and a double strand DNA template was obtained thereby. After the first PCR, 1 µl of amplicon was used as DNA template to conduct the second PCR, and 4 µl of primers of F1, R2, required dNTPs, reagent and Pfu polymerase were mixed to perform the second PCR. The modified nucleotide sequence SEQ.ID.NO. 1 was synthesized after eight times of PCR as described above.

Signal peptides with KDEL sequence are prepared in the same method illustrated above. The primer sequence is shown as K3F AND K3R in table 1. The peptide sequence of the synthesized KDEL is SEQ.ID.NO. 2.

TABLE 1

| Seq. | Primers | Seq. ID. | Sequence listing |
|---|---|---|---|
| E7 | F1 | 4 | 5'-AGAATTC ATG CAC GGT GAC ACC CCG ACC CTG CAC GAA TAC ATG CTG GAC CTC-3' |
| | R1 | 5 | 5'- C GTA GCA GTA CAG GTC GGT GGT TTC CGG CTG GAG GTC CAG CAT GTA-3' |
| | R2 | 6 | 5'- TTC GTC TTC TTC TTC GGA GGA GTC GTT CAG CTG TTC GTA GCA GTA CAG GTC-3' |
| | R3 | 7 | 5'- GTC CGG TTC AGC CTG ACC AGC CGG ACC GTC GAT TTC GTC TTC TTC-3' |
| | R4 | 8 | 5'-T GCA GCA GAA GGT AAC GAT GTT GTA GTG AGC AGC GTC CGG TTC AGC CTG-3' |
| | R5 | 9 | 5'-CTG AAC GCA CAG ACG CAG GGT GGA GTC GCA TTT GCA GCA GAA GGT AAC-3' |
| | R6 | 10 | 5'- TTC CAG GGT ACG GAT GTC AAC GTG GGT GGA CTG AAC GCA CAG ACG-3' |
| | R7 | 11 | 5'- AAC GAT ACC CAG GGT ACC CAT CAG CAG GTC TTC CAG GGT ACG GAT-3' |
| | R8 | 12 | 5'- TTT GAA TTC CGG TTT CTG GGA GCA GAT CGG GCA AAC GAT ACC CAG GGT AC-3' |
| KDEL | K3F | 13 | 5'- AGAATTCGTCGAC TAC CTC AAA AAA GAC GAA CTG AGA GAT GAA CTG-3' |
| | K3R | 14 | 5'-GTG GTG GTG CTC GAG TCA TTA CAG TTC GTC TTT CAG TTC ATC TCT CAG TT-3' |

EXAMPLE 2

Vector Construction of Plasmids

The E7 product obtained from PCR in example 1 is separated by 5% polyacrylamide agarose gel. The target product is purified according to the molecular weight of the product. VectorVectors pET or Ppe (ΔIII) are provided (J. R. Chen, C. W. Liao, S, J. T. Mao, and C. N. Weng, Vet. Microbiol. 80 (2001) 347-357) and digested with restriction endonuclease as well as vector the purified E7. Another electrophoresis is conducted with 5% polyacrylamide agarose gel for further isolating and purifying. Then 0.3 kb of E7 sequence fragment is obtained. 7.84 kb plasmid PE (ΔIII) is further constructed by ligasing the E7 fragment and the vectorvector, which comprises exotoxin A (ETA) but without enzyme toxic section. Moreover, a plasmid pPE (ΔIII)-E7 containing the fusion protein PE(ΔIII)-E7, and a 3.83 kb plasmid pE7 containing E7 fragment and pET23a are also constructed.

A 3.78 kb pKDEL3 plasmid which encodes n'-KDEL-RDELKDEL polypeptide fragment is obtained by digesting, purifying the amplicon (obtained from PCR with K3-F, and K3-R primers), and further inserting into the site of Sall-Xhol of vector pET23a.

Figure 1:
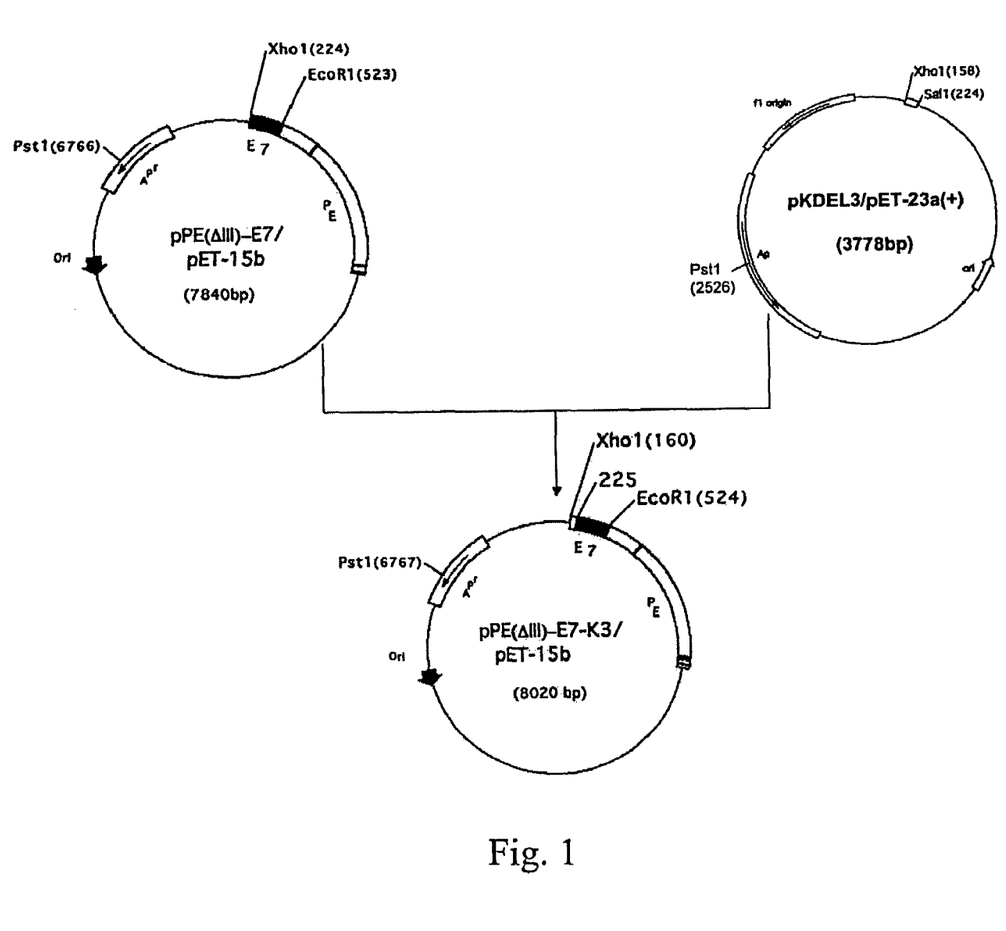

A 8.0 kb plasmid pPE(DIII)-E7-K3 encoding fusion protein PE (ΔIII)-E7-K3 is obtained by digesting 1.47 kb KDEL sequence from pKDEL3 plasmid by restriction endonuclease Sall and Pstl, and further inserting into the spliced 6.5 kb, PE (ΔIII)-E7 plasmid DNA which is spliced by splicing by Xholl and Pstl. The flow chart of preparing plasmid mentioned above is as shown in FIG. 1.

The plasmid constructed above is further transformed to E. coli and maintained in the bacteria strain JM108.

EXAMPLE 3

VectorVectorVector Purification of Protein

The plasmid synthesized above is further transformed into E. coli BL21 (DE3) pLys strain. The transformed E. coli BL21 (DE3) pLys strain is cultured in the 200 ml LB culture medium containing 200 µg/ml ampicillin until the culture concentration reach 0.3 under OD550 spectrum. Then after 1 mM IPTG (isopropylthio-β-D-galactoside, Promege, USA) is added, the E. coli BL21 (DE3) pLys strain is cultured for 2 hours. The grown cells are collected by centrifugation. A freeze-thaw method is conducted to the target protein contained cells to loose the structure of cell membrane. 10 ml lysis buffer (0.3 mg/ml lysozyme, 1 mM PMSF and 0.06 mg/ml DNAse I) is added to the cultured cells, and then placed at room temperature for 20 minutes. 1 ml 10% Triton X-100 is added, and placed at room temperature for 10 minutes. The target proteins are released and collected by centrifugation at a rate of 1200×g for 10 minutes, resulting pallet was washed with 1M or 2M urea. At the end, the collected protein of inclusion body is dissolved in 8 ml 8M urea.

The fusion proteins were then purified under the His-Tag system in the denatured condition as the manufacturer's manual (Novagen, USA). The denatured samples in 8M urea were loaded into a column packed with a NTA-Ni$^{2+}$-bind agarose resin. The bound proteins were then eluted with different pH buffer (from 8.0, 7.0, 6.5, 6.0, 5, 4, and 3.5) containing 6M urea, 0.3M NaCl, and 20 mM Tris-HCL and 20 mM phosphate buffer. After purified, protein elution fractions were analyzed for the purity and quantification by SDS-PAGE analysis as described previously. The purified protein product contained the amino acid sequence as shown in SQE:ID.NO. 3.

EXAMPLE 4

Preparing Carcinoma Cell Strain (TC-1)

HPV16 E6, E7 and ras oncogene were used to transform primary lung epithelial cells of C57BL/6 mice. This tumorigenic cell line was named TC-1. TC-1 cells were grown in RPMI 1640, supplemented with 10% (vol/vol) fetal bovine serum, 50 units/ml penicillin/streptomycin, 2 mM L-glutamine, 1 mM sodium pyruvate, 2 mM nonessential amino acids and 0.4 mg/ml G418 at 37° C. with 5% $CO_2$. On the day of tumor challenge, tumor cells were harvested by trypsinization, washed twice with 1× Hanks buffered salt solution (HBSS) and finally resuspended in 1×HBSS to the designated concentration for injection.

EXAMPLE 5

In Vivo Tumor Protection Experiments

The testing protein samples: E7, PE (ΔIII), PE (ΔIII)-E7, PE (ΔIII)-E7-KDEL3 are diluted with a phosphate buffer solution in a ratio of 1:10 to make the concentration at 0.1 mg/ml. Then the test samples are incubated at 37° C. for 2 hours. The incubated samples are mixed with 10% ISA206 (Sepec, France) by a vortex to form 4 kinds of different vaccines. Then 0.1 mg of each vaccine obtained is injected to the mice for vaccination. These mice were then boosted subcutaneously two weeks later with the same regimen as the first vaccination. One week after last vaccination, mice were challenged with $5 \times 10^4$ TC-1 tumor cells by subcutaneous injection in the right leg. Naive mice received the same amount of TC-1 cells to assess natural tumor growth control. Tumor growth was monitored by visual inspection and palpation twice weekly until 7, 14, 20, 30, and 60 days after after tumor challenge. The spleens of the sacrificed mice are also taken out for further checking.

Figure 2:
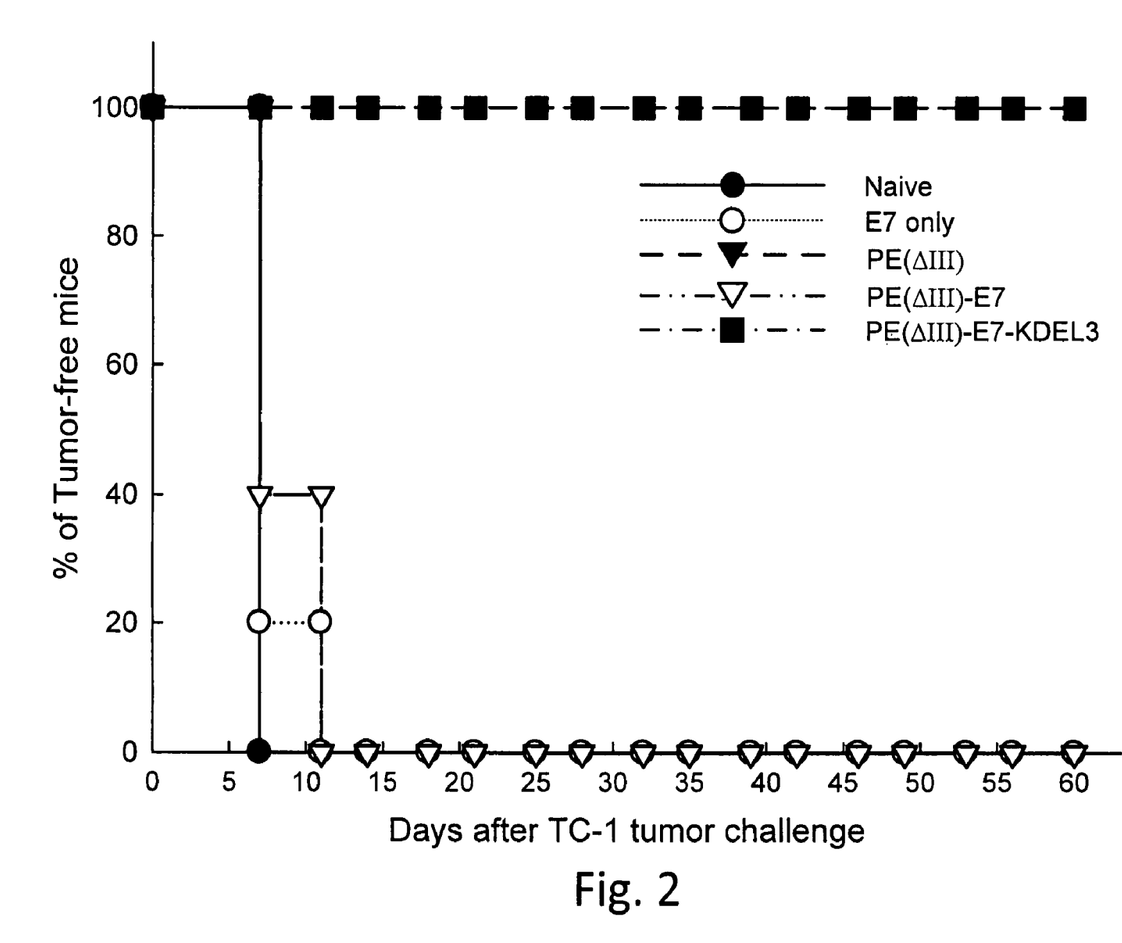

As shown in FIG. 2, no cancer cells are found in the mice injected with PE (ΔIII)-E7-KDEL3. In other words, the percentage of the PE (ΔIII)-E7-KDEL3-injected mice without cancer cells is 100%. Moreover, even 60 days later, none of the PE (ΔIII)-E7-KDEL3-injected mice has cancer. In contrary, cancer cells can be found in the mice injected with E7, PE (ΔIII), or PE (ΔIII)-E7, or the mice of control. The longest period without cancer cells among these mice is 20 days. According to the result of the experiment, only fusion protein include the sequence of PE (ΔIII), and KDEL3, and the fragment of E7 can prevent and inhibit the growth of cancer cells in the cancer-inducing model illustrated above.

EXAMPLE 6

Cell Immune Experiment

Mice are injected, and cancer-induced as described in example 5. One week later, the mice are sacrificed and the spleen macrophages are taken out. Before intracellular cytokine staining, $3.5 \times 10^5$ pooled splenocytes from each vaccinated group were incubated for 16 hours with either 1 μg/ml of E7 peptide (aa 49-57) containing an MHC class I epitope for detecting E7-specific CD8$^+$ T cell precursors. Cell surface marker staining of CD8$^+$ or CD4$^+$ and intracellular cytokine staining for IFN-γ, as well as FACScan analysis, were performed using conditions described by Cheng, et al. (Hum Gene Ther, 13:553-568, 2002) to compare the E7-sepcific immunological assays in mice received different regimens of vaccination.

Figure 3:
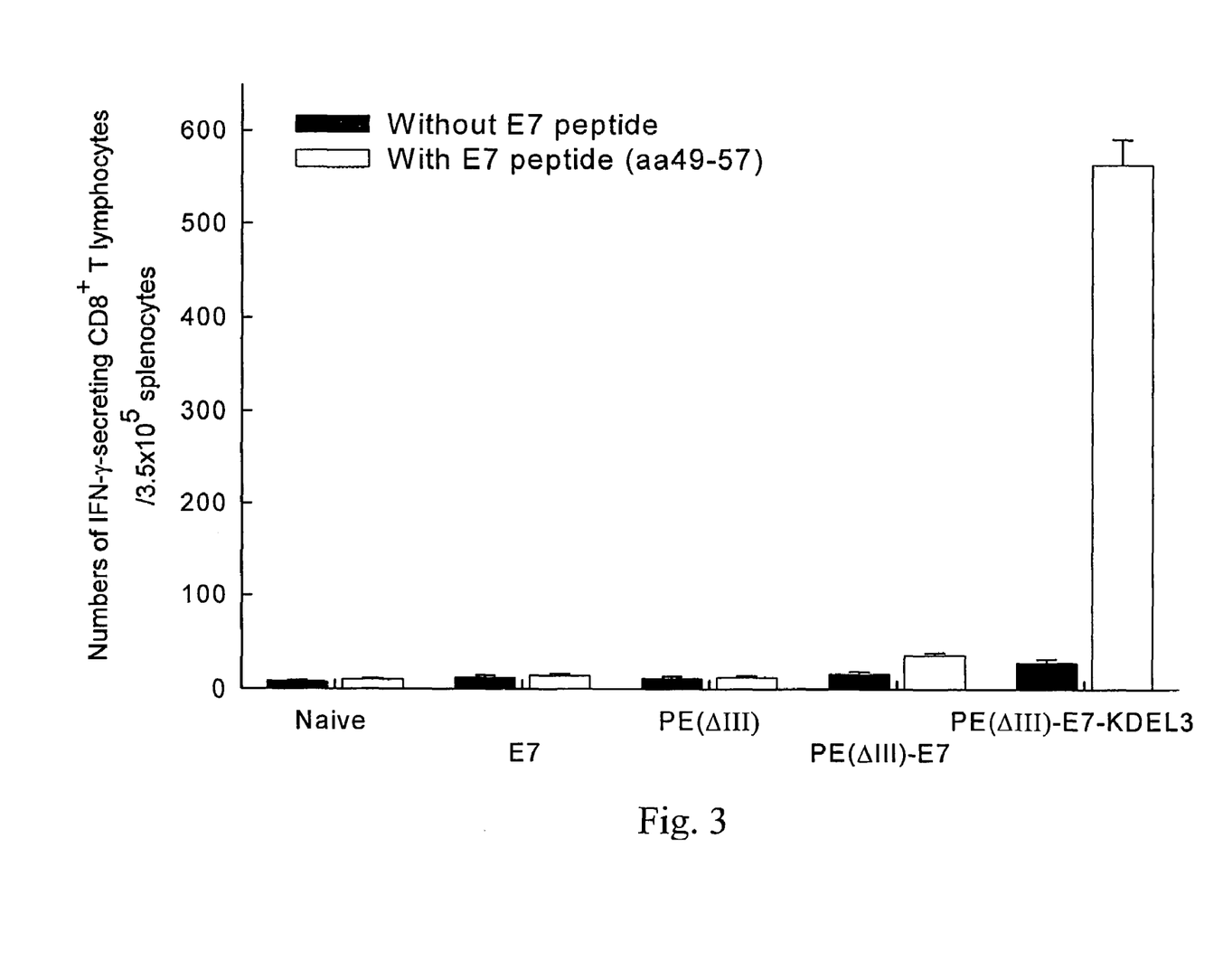

In the present example, it is confirmed that PE (ΔIII)-E7-KDEL3 has influence for E7 specific immunization, as shown in FIG. 3. In the mice of the group injected with PE (ΔIII)-E7-KDEL3, it is founded that the numbers of E7-specific IFN-γ-secreting CD8$^+$ T cell precursors in PE(ΔIII)-E7-KDEL3 group were higher than those in the other groups (10.0±1.4 in naïve group, 14.0±2.1 in E7 group, 12.0±2.1 in PE(ΔIII) group, 36.0±2.8 in PE(ΔIII)-E7 group, 564.0±28.0 in PE(ΔIII)-E7-KDEL3, p<0.01, AVONA).

According to the result above, the number of E7-specific IFN-γ(+) CD8(+) T cell precursors of the mice vaccinated with PE(ΔIII)-E7-KDEL3 protein is 40 times higher than that vaccinated with E7.

EXAMPLE 7

E7 Specific Antibody Evaluation

Mice are vaccinated with 0.1 mg of the E7, PE (ΔIII), PE (ΔIII)-E7, PE (ΔIII)-E7-KDEL3 fusion proteins as described in example 5. Further boosts after one and two weeks later with the same regimen as the first vaccination are conducted. The mouse serum is collected at the 7$^{th}$ day after the last immunization.

Briefly, a 96-microwell plate was coated with 100 μl of bacteria-derived HPV-16 E7 proteins (0.5 μg/ml) and incubated at 4° C. overnight. The wells were then blocked with phosphate-buffered saline (PBS) containing 20% feta bovine serum. Sera were prepared from mice of various vaccinated groupd serially diluted in PBS, added to the ELISA wells, and incubated at 37° C. for 2 hr. After washing with PBS containing 0.05% Tween 20, the plate was incubated with a 1:2000 dilution of a peroxidase-conjugated rabbit anti-mouse IgG antibody (Zymed, San Francisco, Calif.) at room temperature for 1 hr. The plate was washed, developed with 1-Step Turbo TMB-ELISA (Pierce, Rockford, Ill.), and stopped with 1 M $H_2SO4$. The ELISA plate was read with a standard ELISA reader at 450 nm.

C57BL/6 mice were immunized subcutaneously with PE(ΔIII)-E7-KDEL3 mixed 10% ISA206 adjuvant one to three times. Sera were prepared and the E7-specific antibody titers were detected by the ELISA as described earlier.

Figure 4:
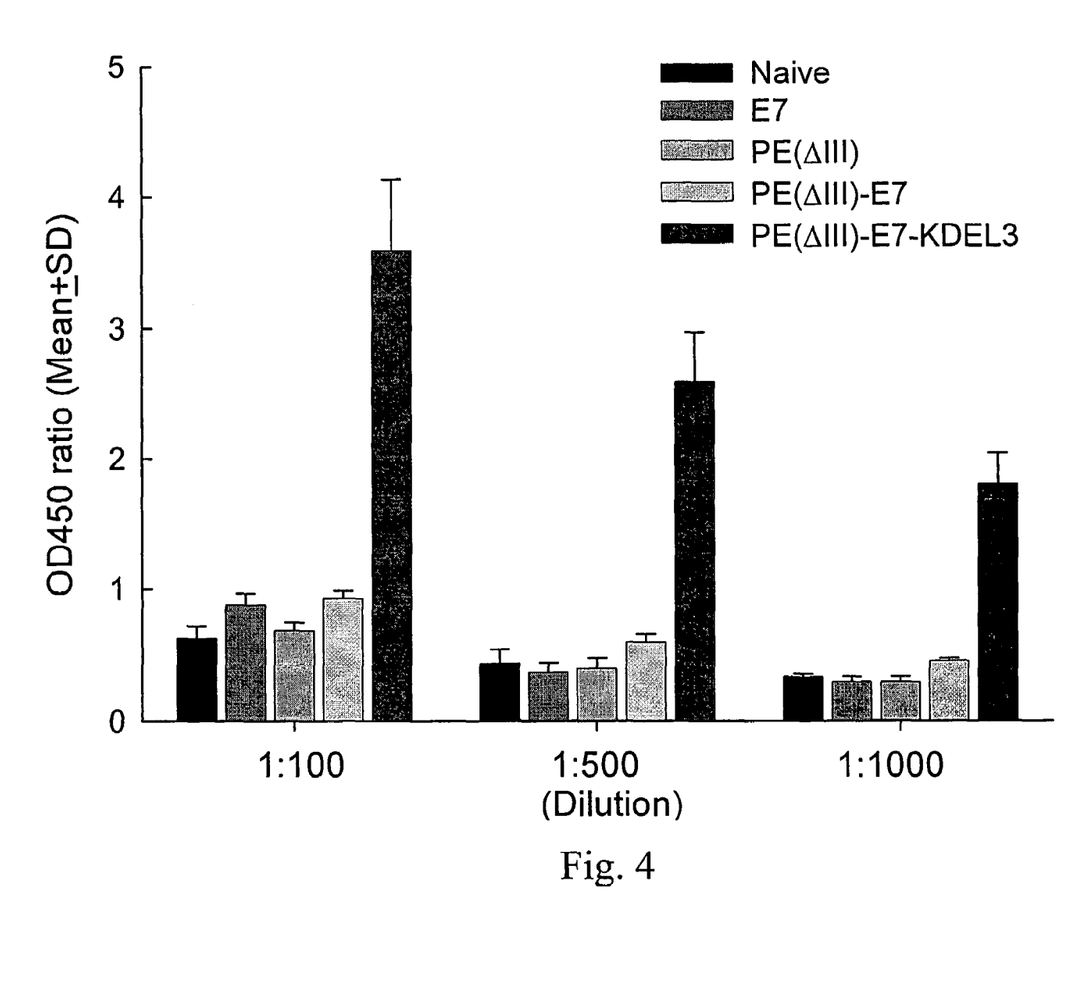

In the present example, it is further confirmed that PE (ΔIII)-E7-KDEL3 is able to improve the potency of resisting E7 antibody. As shown in FIG. 4, mice vaccinated with the PE(ΔIII)-KDEL/E7 protein generate highest titers of anti-E7 Ab's in the sera of mice compared with those vaccinated with other fusion protein (for 1:100 dilution, 0.629±0.093 in naïve group, 0.882±0.086 in E7 group, 0.690±0.06 in PE(ΔIII) group, 0.930±2.80.06 in PE(ΔIII)-E7 group, 3.593±0.54 in PE(ΔIII)-E7-KDEL3, p<0.01, AVONA). Apparently, PE(ΔIII)-E7-KDEL3 protein could also enhance the titer of anti-E7 antibody.

The data showed that PE(ΔIII)-E7-KDEL3 fusion protein could enhance E7-specific immunological responses (including the numbers of E7-specific CD4$^+$ and CD8$^+$ T lymphocytes and the titers of E7-specific antibodies).

All the obtained readings are expressed with Mean Value and Mean±SEM. The compared data from the experiment will be processed ANOVA analysis by Statistical Package for Social Sciences, SPSS 9.0, SPSS Inc, Chicago, Ill.; there is a significant difference of the data if the statistical error is under 0.05.

EXAMPLE 8

Application of an Adjuvant in a Vaccine Composition

In many cases, peptides or proteins are poorly immunogenic and hardly induce a response when they injected alone. Hence, an adjuvant is usually injected together with peptides or proteins. Examples of such adjuvants include BCG, incomplete Freund's adjuvant, cwellra toxin B, GM-CSF, ISA206 and IL-12, wherein ISA206 is used for the protein adjuvant of the present embodiment.

Figure 5:
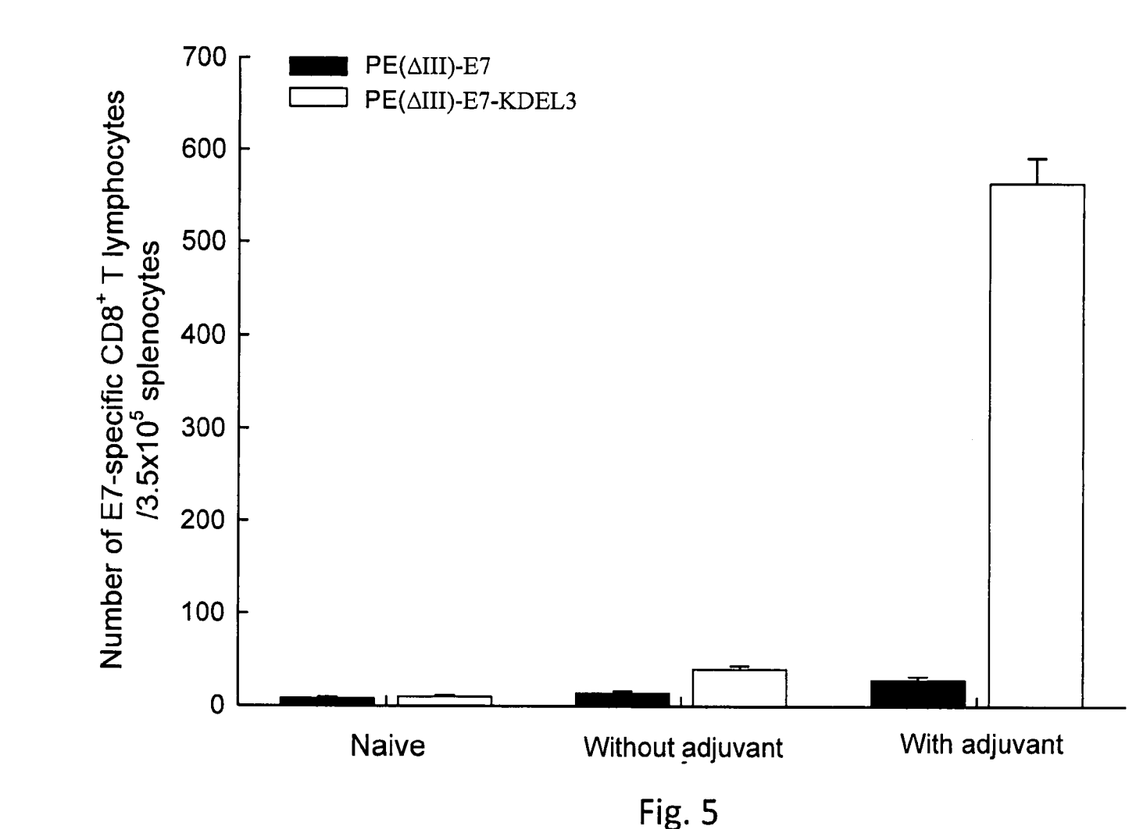

The fusion proteins here are PE (ΔIII)-E7, and PE (ΔIII)-E7-KDEL3. The process of mice vaccination was the same as that described above in examples 5 and 6. Samples of fusion proteins were mixed with or without 10% ISA206 adjuvant (SEPPIC, France). The result is shown in FIG. 5, wherein the first sample group (i.e. the blank sample group) showed no significant immune response for E7 specific CD 8+ T lymphocytes stimulation. The same result can be found in the second sample group. In other words, no matter E7 is included in the vaccine or not, there is no significant numbers of antibody induced by the vaccine composition without adjuvants. However, the numbers of E7 specific CD 8+ T lymphocytes is about 600, which is 500-600 times higher than that induced by the vaccine composition without adjuvant.

Figure 6:
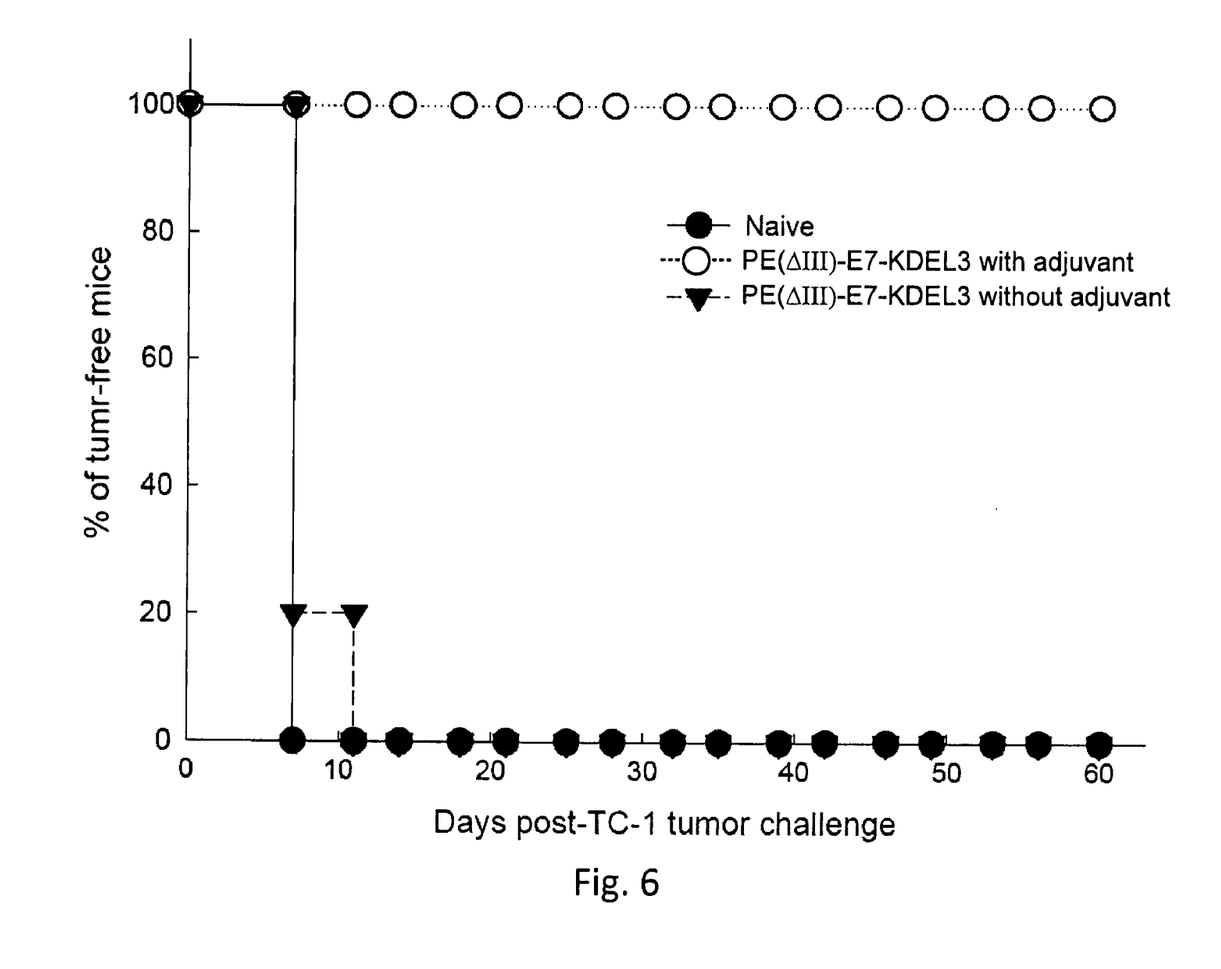

As shown in FIG. 6, the period for preventing the proliferation of cancer in the induced mice by administrating (through injection) the mice with the vaccine composition having PE (ΔIII)-E7-KDEL3 and adjuvant is 60 days. In contrary, for the mice administrated with the vaccine composition of PE (ΔIII)-E7-KDEL3 without an adjuvant, the population of the mice with tumor is almost the same as that of the control group which is not vaccinated with fusion proteins of the present invention. Mice immunized with PE(ΔIII)-E7-KDEL3 protein alone (i.e. without an adjuvant) could not generate potent E7-specific immunological responses and anti-tumor effects (data not shown). However, according to the result, vaccine compositions of PE(ΔIII)-E7-KDEL3 protein of the present invention comprising an adjuvant is preferred for application for capability to induce optimal immunological responses.

EXAMPLE 9

In vivo tumor treatment experiments were performed using a lung hematogenous spread model. C57BL/6 mice mice (five per group) were challenged with $5 \times 10^4$ cells/mouse TC-1 tumor cells via tail vein. Two days after tumor challenge, mice received 0.1 mg/mouse of E7, PE(ΔIII), PE(ΔIII)-E7 or PE(ΔIII)-E7-KDEL3 protein vaccines subcutaneously, followed by a booster with the same regimen every 7 days for 2 weeks (a total of four times, 0.3 mg protein). Mice receiving no vaccination were used as a negative control. Mice were sacrificed and lungs were explanted on day 30. The pulmonary tumor nodules in each mouse were evaluated and counted by experimenters blinded to sample identity.

Figure 7A:
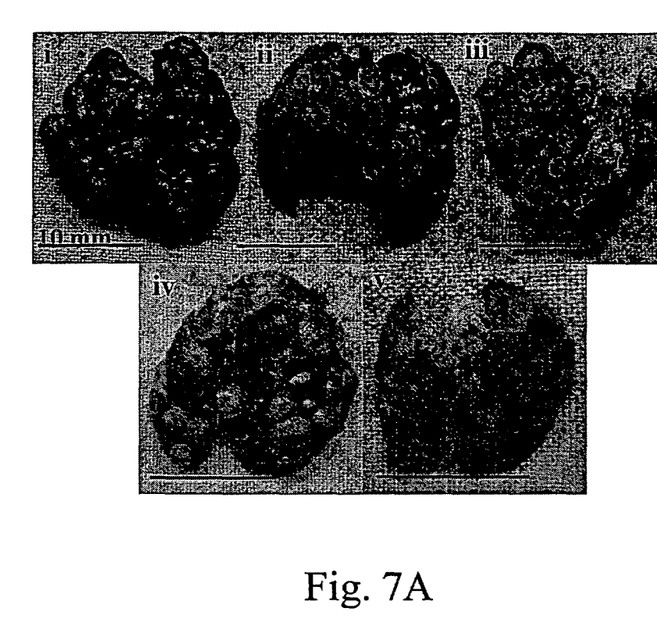
Figure 7B:
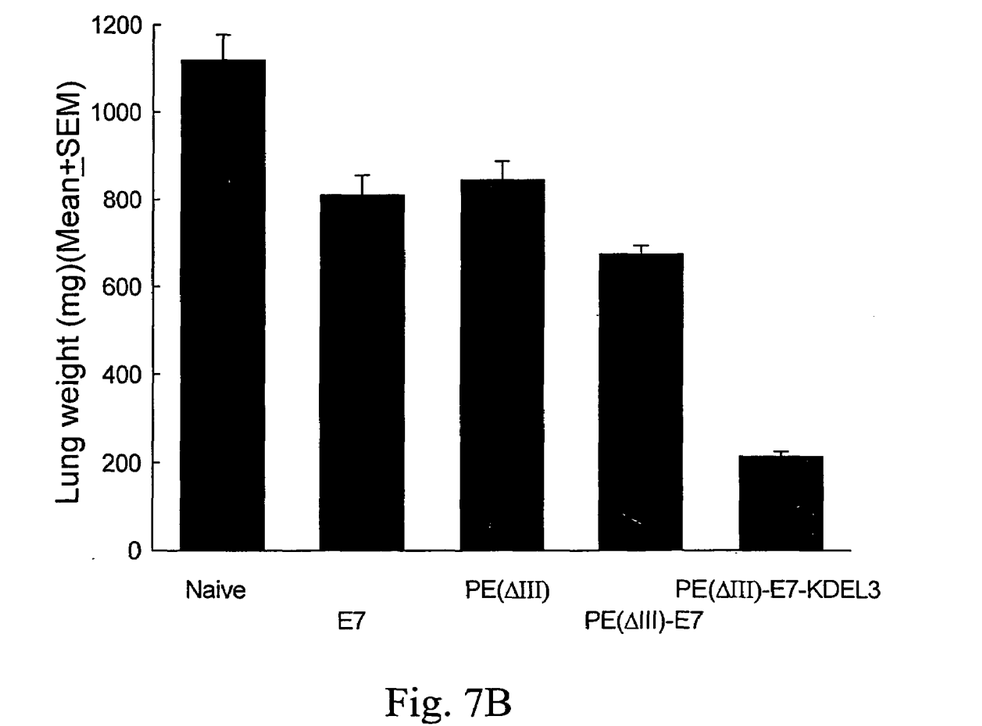

The representative figures of pulmonary tumor nodules in various protein-vaccinated groups are shown in FIGS. 7A and 7B. As shown in FIG. 7A, only the mice accepting the PE(ΔIII)-E7-KDEL3 fusion protein don't have lung cancer. The mean lung weight (214.4±11.6) of the mice treated with PE(ΔIII)-E7-KDEL3 showed significantly lower than those of mice treated with PE(ΔIII)-E7 (673.6±20.8) or wild-type E7 protein (811.1±45.6) (one-way ANOVA, p<0.001) These data indicated that mice treated with PE(ΔIII)-E7-KDEL3 could control established E7-expressing tumors in the lungs.

EXAMPLE 10

Evaluation of the E7-specific immunological profiles of the mice immunized with different times of PE(ΔIII)-E7-KDEL3 protein vaccine could reflect the anti tumor effects of the mice. As described earlier in examples 5 and 6, mice were challenged with TC-1 tumor cells and then received 0.1 mg PE(ΔIII)-E7-KDEL3 protein from one to three times as described earlier. Mice were sacrificed on day 30 and the pulmonary tumor nodules in each mouse were evaluated and counted as described earlier.

Figure 8A:
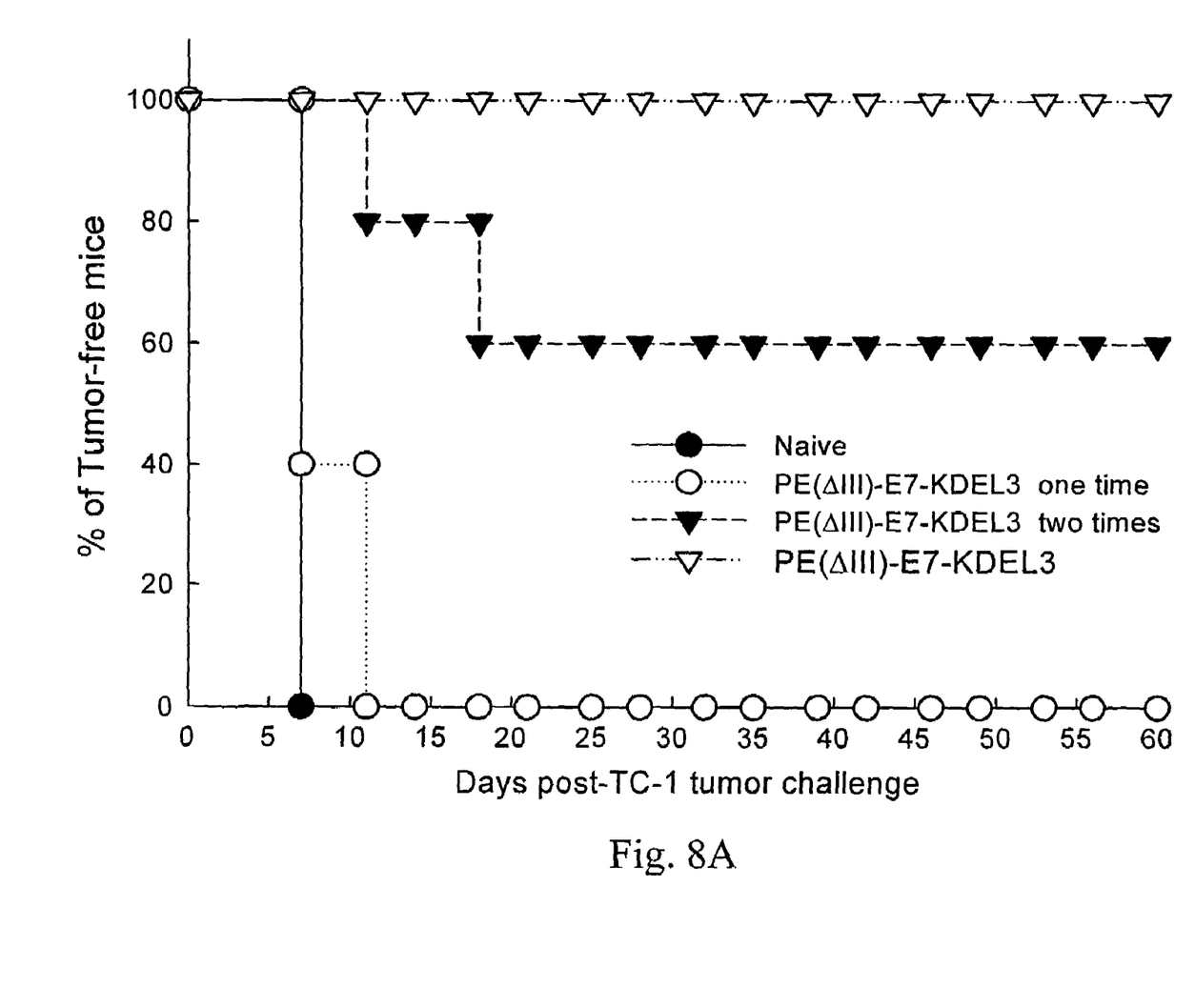
Figure 8B:
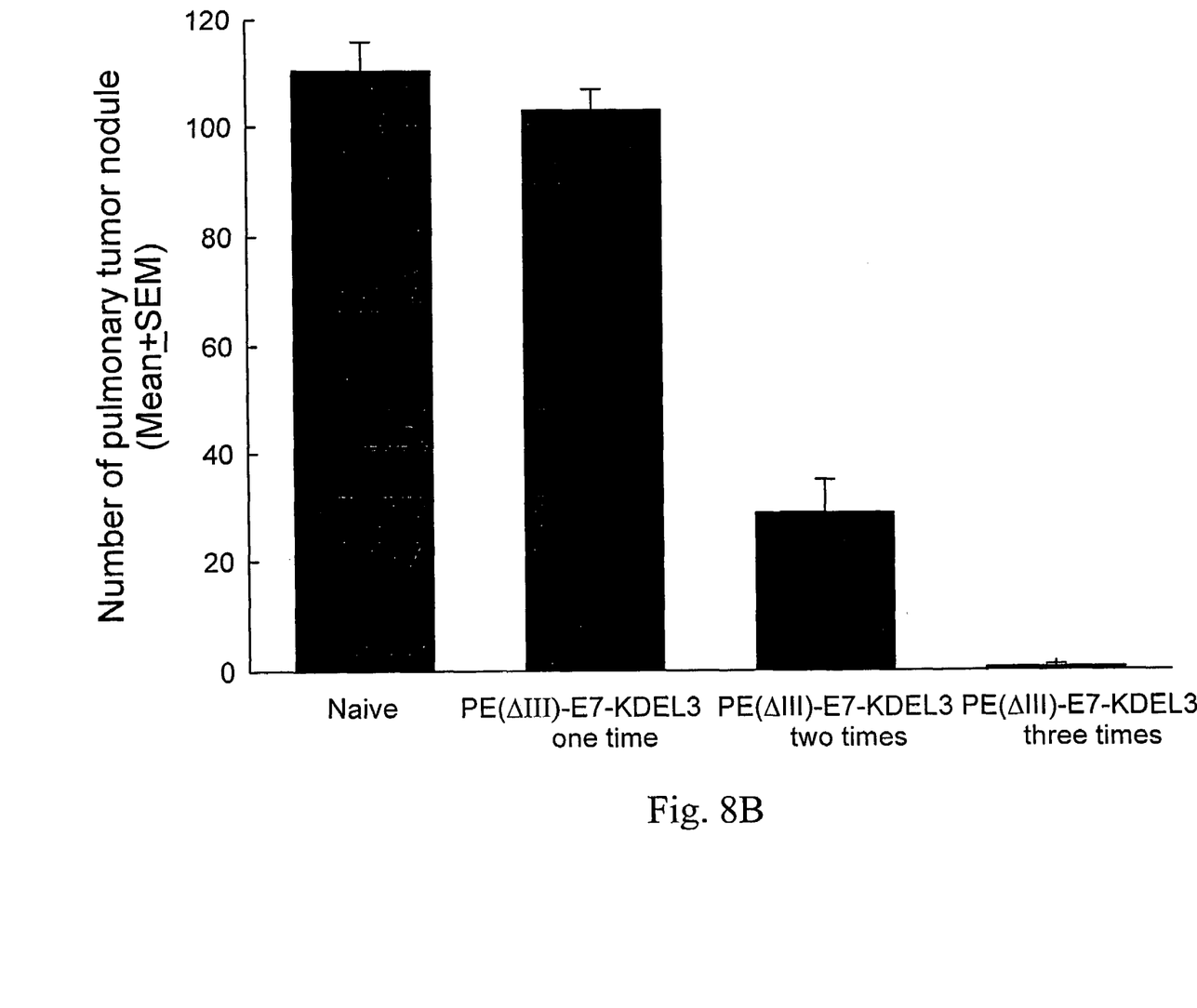

As shown in FIG. 8A, all of the naïve mice and mice immunized one time of PE(ΔIII)-KDEL3 protein vaccine grew tumors within 14 days after tumor cell TC-1 challenged. And 60% or 100% of mice immunized with 2 or 3 times of PE(ΔIII)-KDEL3 protein vaccine were tumor-free 60 days after tumor challenge, respectively.

Similar phenomena were also observed in the tumor treatment experiments as described in example 9. The pulmonary tumor nodules decreased significantly from one to three shots of PE(ΔIII)-KDEL3 protein vaccine (103.0±3.8 for one time, 28.8±6.1 for two times, 0.6±0.4 for three times, p<0.001, ANOVA)

Our results show that increasing shots of PE(ΔIII)-KDEL3 protein vaccine could improve the preventive and therapeutic anti-tumor effects of E7-expressing tumor cells.

PE(ΔIII)-E7-KDEL protein could enhance MHC class I presentation of E7 in cells expressing this fusion protein to enhance E7-specific CD8+ T-cell activity in vivo.

According to the examples illustrated above, the fusion protein of the present invention can enhance the stimulation of the precursor of E7 specific CD 8+ T lymphocytes and CD 4+ T lymphocytes by enhancing the presentation of the E7 antigen through MHC I and II. The concentration of the E7 specific antibody can be increased through the mechanism illustrated above. Moreover, the cancer induced by E7 can be inhibited or prevented through the administration of the fusion protein of the present invention. In addition, the mice vaccinated by the fusion protein of the present invention have longer time for inhibiting cancer.

Although the present invention has been explained in relation to its preferred embodiment, it is to be understood that many other possible modifications and variations can be made without departing from the spirit and scope of the invention as hereinafter claimed.

SEQUENCE LISTING

<160> NUMBER OF SEQ ID NOS: 14

<210> SEQ ID NO 1
<211> LENGTH: 310

```
<212> TYPE: DNA
<213> ORGANISM: Human papillomavirus type 16

<400> SEQUENCE: 1
ggaattcatg cacggtgaca ccccgaccct gcacgaatac atgctggacc tccagccgga      60
aaccaccgac ctgtactgct acgaacagct gaacgactcc tccgaagaag aagacgaaat     120
cgacggtccg gctggtcagg ctgaaccgga ccgtgctcac tacaacatcg ttaccttctg     180
ctgcaaatgc gactccaccc tgctgctgtg cgttcagtcc acccacgttg acatccgtac     240
cctggaagac ctgctgatgg gtaccctggg tatcgtttgc ccgatctgct cccagaaacc     300
gctcgagaaa                                                            310

<210> SEQ ID NO 2
<211> LENGTH: 18
<212> TYPE: PRT
<213> ORGANISM: Pseudomonas sp.

<400> SEQUENCE: 2

Lys Leu Asp Tyr Leu Lys Lys Asp Glu Leu Arg Asp Glu Leu Lys Asp
1               5                   10                  15

Glu Leu

<210> SEQ ID NO 3
<211> LENGTH: 158
<212> TYPE: PRT
<213> ORGANISM: Human papillomavirus type 16

<400> SEQUENCE: 3

Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
                20                  25                  30

Ile Ile Leu Glu Cys Val Tyr Cys Lys Gln Gln Leu Leu Arg Arg Glu
            35                  40                  45

Val Tyr Asp Phe Ala Phe Arg Asp Leu Cys Ile Val Tyr Arg Asp Gly
    50                  55                  60

Asn Pro Tyr Ala Val Cys Asp Lys Cys Leu Lys Phe Tyr Ser Lys Ile
65                  70                  75                  80

Ser Glu Tyr Arg His Tyr Cys Tyr Ser Leu Tyr Gly Thr Thr Leu Glu
                85                  90                  95

Gln Gln Tyr Asn Lys Pro Leu Cys Asp Leu Leu Ile Arg Cys Ile Asn
            100                 105                 110

Cys Gln Lys Pro Leu Cys Pro Glu Glu Lys Gln Arg His Leu Asp Lys
        115                 120                 125

Lys Gln Arg Phe His Asn Ile Arg Gly Arg Trp Thr Gly Arg Cys Met
    130                 135                 140

Ser Cys Cys Arg Ser Ser Arg Thr Arg Arg Glu Thr Gln Leu
145                 150                 155

<210> SEQ ID NO 4
<211> LENGTH: 52
<212> TYPE: DNA
<213> ORGANISM: Artificial
<220> FEATURE:
<223> OTHER INFORMATION: artificial primer for E7 peptide.

<400> SEQUENCE: 4
agaattcatg cacggtgaca ccccgaccct gcacgaatac atgctggacc tc             52
```

<210> SEQ ID NO 5
<211> LENGTH: 46
<212> TYPE: DNA
<213> ORGANISM: Artificial
<220> FEATURE:
<223> OTHER INFORMATION: artificial primer for E7 peptide.

<400> SEQUENCE: 5
cgtagcagta caggtcggtg gtttccggct ggaggtccag catgta          46

<210> SEQ ID NO 6
<211> LENGTH: 51
<212> TYPE: DNA
<213> ORGANISM: Artificial
<220> FEATURE:
<223> OTHER INFORMATION: artificial primer for E7 peptide.

<400> SEQUENCE: 6
ttcgtcttct tcttcggagg agtcgttcag ctgttcgtag cagtacaggt c          51

<210> SEQ ID NO 7
<211> LENGTH: 48
<212> TYPE: DNA
<213> ORGANISM: Artificial
<220> FEATURE:
<223> OTHER INFORMATION: artificial primer for E7 peptide.

<400> SEQUENCE: 7
gtccggttca gcctgaccag ccggaccgtc gatttcgtct tcttcttc          48

<210> SEQ ID NO 8
<211> LENGTH: 49
<212> TYPE: DNA
<213> ORGANISM: Artificial
<220> FEATURE:
<223> OTHER INFORMATION: artificial primer for E7 peptide.

<400> SEQUENCE: 8
tgcagcagaa ggtaacgatg ttgtagtgag cagcgtccgg ttcagcctg          49

<210> SEQ ID NO 9
<211> LENGTH: 48
<212> TYPE: DNA
<213> ORGANISM: Artificial
<220> FEATURE:
<223> OTHER INFORMATION: artificial primer for E7 peptide.

<400> SEQUENCE: 9
ctgaacgcac agacgcaggg tggagtcgca tttgcagcag aaggtaac          48

<210> SEQ ID NO 10
<211> LENGTH: 45
<212> TYPE: DNA
<213> ORGANISM: Artificial
<220> FEATURE:
<223> OTHER INFORMATION: artificial primer for E7 peptide.

<400> SEQUENCE: 10
ttccagggta cggatgtcaa cgtgggtgga ctgaacgcac agacg          45

<210> SEQ ID NO 11
<211> LENGTH: 46
<212> TYPE: DNA
<213> ORGANISM: Artificial
<220> FEATURE:

-continued

```
<223> OTHER INFORMATION: artificial primer for E7 peptide.

<400> SEQUENCE: 11 aacgatacccc agggtaccca tcagcaggtc ttccagggta cggatv              46

<210> SEQ ID NO 12
<211> LENGTH: 50
<212> TYPE: DNA
<213> ORGANISM: Artificial
<220> FEATURE:
<223> OTHER INFORMATION: artificial primer for E7 peptide.

<400> SEQUENCE: 12
tttgaattcc ggtttctggg agcagatcgg gcaaacgata cccagggtac           50

<210> SEQ ID NO 13
<211> LENGTH: 46
<212> TYPE: DNA
<213> ORGANISM: Artificial
<220> FEATURE:
<223> OTHER INFORMATION: artificial primer for KDEL.

<400> SEQUENCE: 13
agaattcgtc gactacctca aaaaagacga actgagagat gaactg               46

<210> SEQ ID NO 14
<211> LENGTH: 50
<212> TYPE: DNA
<213> ORGANISM: Artificial
<220> FEATURE:
<223> OTHER INFORMATION: artificial primer for KDEL.

<400> SEQUENCE: 14
gtggtggtgc tcgagtcatt acagttcgtc tttcagttca tctctcagtt           50
```

What is claimed is:

1. A fusion protein for inhibiting cancer induced by human papillomavirus type 16, comprising:
   an E7 peptide sequence of human papillomavirus type 16;
   a translocating peptide for translocation; and
   a carboxyl terminal section comprising an amino acid sequence selected from the group consisting of KDEL, KDELRDELKDEL and SEQ ID NO: 2.

2. The fusion protein of claim 1, wherein the carboxyl terminal section comprises an amino acid sequence KDEL-RDELKDEL.

3. The fusion protein of claim 1, wherein said E7 peptide sequence of human papillomavirus type 16 comprises an amino acid sequence set forth by SEQ. ID. NO. 3.

4. The fusion protein of claim 1, wherein said translocating peptide is from pseudomonas exotoxin.

5. The fusion protein of claim 1, wherein the translocating peptide comprises a pseudomonas exotoxin A fragment deleted of only domain III.

6. The fusion protein of claim 1, wherein said carboxyl terminal section comprises amino acid sequence KDEL.

7. A fusion protein for inhibiting cancer induced by human papillomavirus type 16, comprising:
   a. an E7 eptide sequence of human papillomavirus type 16;
   b. a translocating peptide for translocation; and
   c. a carboxyl terminal section comprising an amino acid sequence set forth by SEQ ID NO: 2.

8. A pharmaceutical composition for suppressing cancer induced by human papillomavirus type 16, comprising an effective amount of a fusion protein of claim 1 and an adjuvant.

9. A pharmaceutical composition for inhibiting cancer induced by human papillomavirus type 16, comprising an effective amount of a fusion protein of claim 2 and an adjuvant.

10. A pharmaceutical composition for inhibiting cancer induced by human papillomavirus type 16, comprising an effective amount of a fusion protein of claim 3 and an adjuvant.

11. A pharmaceutical composition for suppressing cancer induced by human papillomavirus type 16, comprising an effective amount of a fusion protein of claim 5 and an adjuvant.

12. A pharmaceutical composition for suppressing cancer induced by human papillomavirus type 16 comprising an effective amount of a fusion protein of claim 7 and an adjuvant.

13. A method of suppressing cancer caused by human papillomavirus type 16 in a subject in need thereof, comprising the step of administering to the subject an effective amount of the pharmaceutical composition of claim 8.

14. A method of suppressing cancer caused by human papillomavirus type 16 in a subject in need thereof, comprising the step of administering to the subject an effective amount of the pharmaceutical composition of claim 9.

15. A method of suppressing cancer caused by human papillomavirus type 16 in a subject in need thereof, comprising the step of administering to the subject an effective amount of the pharmaceutical composition of claim 10.

16. A method of suppressing cancer caused by human papillomavirus type 16 in a subject in need thereof, comprising the step of administering to the subject an effective amount of the pharmaceutical composition of claim 11.

17. A method of suppressing cancer caused by human papillomavirus type 16 in a subject in need thereof, comprising the step of administering to the subject an effective amount of the pharmaceutical composition of claim 12.

18. The method of claim 13, wherein the step of administering is performed at least three times with a time interval between each administering step.

19. The method of claim 14, wherein the step of administering is performed at least three times with a time interval between each administering step.

20. The pharmaceutical composition of claim 8, wherein the adjuvant is ISA 206.

21. The method of claim 15, wherein the step of administering is performed at least three times with a time interval between each administering step.

22. The method of claim 16, wherein the step of administering is performed at least three times with a time interval between each administering step.

* * * * *

UNITED STATES PATENT AND TRADEMARK OFFICE
CERTIFICATE OF CORRECTION

PATENT NO. : 7,378,100 B2  Page 1 of 1
APPLICATION NO. : 11/206138
DATED : May 27, 2008
INVENTOR(S) : Hsui-Kan Chang, Chao-We Liao and Wen-Fang Cheng It is certified that error appears in the above-identified patent and that said Letters Patent is hereby corrected as shown below:

At column 13, line 17, amend SEQ ID NO: 3 as follows:

```
<210>  3
<211>  98
<212>  Modifed PRT
<213>  Human papillomavirus type 16

<400>  3

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Leu Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
            85                  90                  95

Lys Pro
```

Signed and Sealed this

Nineteenth Day of May, 2009

JOHN DOLL
*Acting Director of the United States Patent and Trademark Office*